(12) United States Patent
Williams et al.

(10) Patent No.: US 9,463,500 B1
(45) Date of Patent: Oct. 11, 2016

(54) DYNAMIC STRINGER FORMING SYSTEM

(71) Applicant: The Boeing Company, Chicago, IL (US)

(72) Inventors: Thomas K. Williams, Federal Way, WA (US); John Willard Dorsey-Palmateer, Gig Harbor, WA (US); Mike Majid Moodi, Bothell, WA (US); Melissa McQueen, Seattle, WA (US)

(73) Assignee: THE BOEING COMPANY, Chicago, IL (US)

( * ) Notice: Subject to any disclaimer, the term of this patent is extended or adjusted under 35 U.S.C. 154(b) by 547 days.

(21) Appl. No.: 13/647,913

(22) Filed: Oct. 9, 2012

(51) Int. Cl.
*B21D 5/00* (2006.01)
*G01N 3/20* (2006.01)

(52) U.S. Cl.
CPC .............. *B21D 5/006* (2013.01); *B21D 5/002* (2013.01); *G01N 3/20* (2013.01)

(58) Field of Classification Search
CPC ........ B21D 5/002; B21D 5/006; B21D 5/02; B21D 5/0209; G01N 3/20
USPC ............... 72/1, 16.1, 16.6, 17.1, 20.1, 30.1, 72/30.04, 31.1, 37, 293, 379.2, 380, 392, 72/394, 411, 417, 452.1, 459, 441, 446, 72/455, 457, 462, 483, 389.3, 389.5, 7.4, 72/173, 18.7, 10, 21, 12, 9, 299, 307, 26, 72/32, 34, 389, 702; 73/853, 849
See application file for complete search history.

(56) References Cited

U.S. PATENT DOCUMENTS

| | | | |
|---|---|---|---|
| 3,949,588 A | | 4/1976 | Seo |
| 4,408,471 A | * | 10/1983 | Gossard .................. B21D 5/006 72/702 |
| 4,511,976 A | * | 4/1985 | Graf ....................... B21D 5/006 72/702 |
| 4,819,467 A | * | 4/1989 | Graf ....................... B21D 5/006 72/702 |
| 4,878,369 A | * | 11/1989 | Apps et al. .................... 72/18.7 |
| 4,947,666 A | | 8/1990 | Hametner et al. |
| 4,972,696 A | * | 11/1990 | Apps et al. .................... 72/16.2 |
| 5,114,230 A | | 5/1992 | Pryor |
| 5,483,750 A | * | 1/1996 | Ooenoki et al. ............. 72/389.3 |
| 5,829,288 A | * | 11/1998 | Serruys .................... B21D 5/02 72/702 |
| 6,539,763 B1 | * | 4/2003 | Chebbi .................... B21D 5/02 72/31.1 |
| 6,708,541 B1 | * | 3/2004 | Matsumoto et al. .......... 72/31.1 |
| 7,325,427 B2 | * | 2/2008 | Ingvarsson ...................... 72/7.4 |
| 7,802,456 B2 | * | 9/2010 | Ikeda ....................... B21D 5/02 72/31.1 |

* cited by examiner

*Primary Examiner* — Shelley Self
*Assistant Examiner* — Mohammad Yusuf
(74) *Attorney, Agent, or Firm* — Yee & Associates, P.C.

(57) ABSTRACT

A method and apparatus for bending an elongate member. A plastic force may be applied to the elongate member. The plastic force may be configured to cause the elongate member to bend with a plastic deformation. The plastic force may be reduced to an elastic force that is applied to the elongate member after the plastic force causes the elongate member to bend with the plastic deformation.

13 Claims, 10 Drawing Sheets

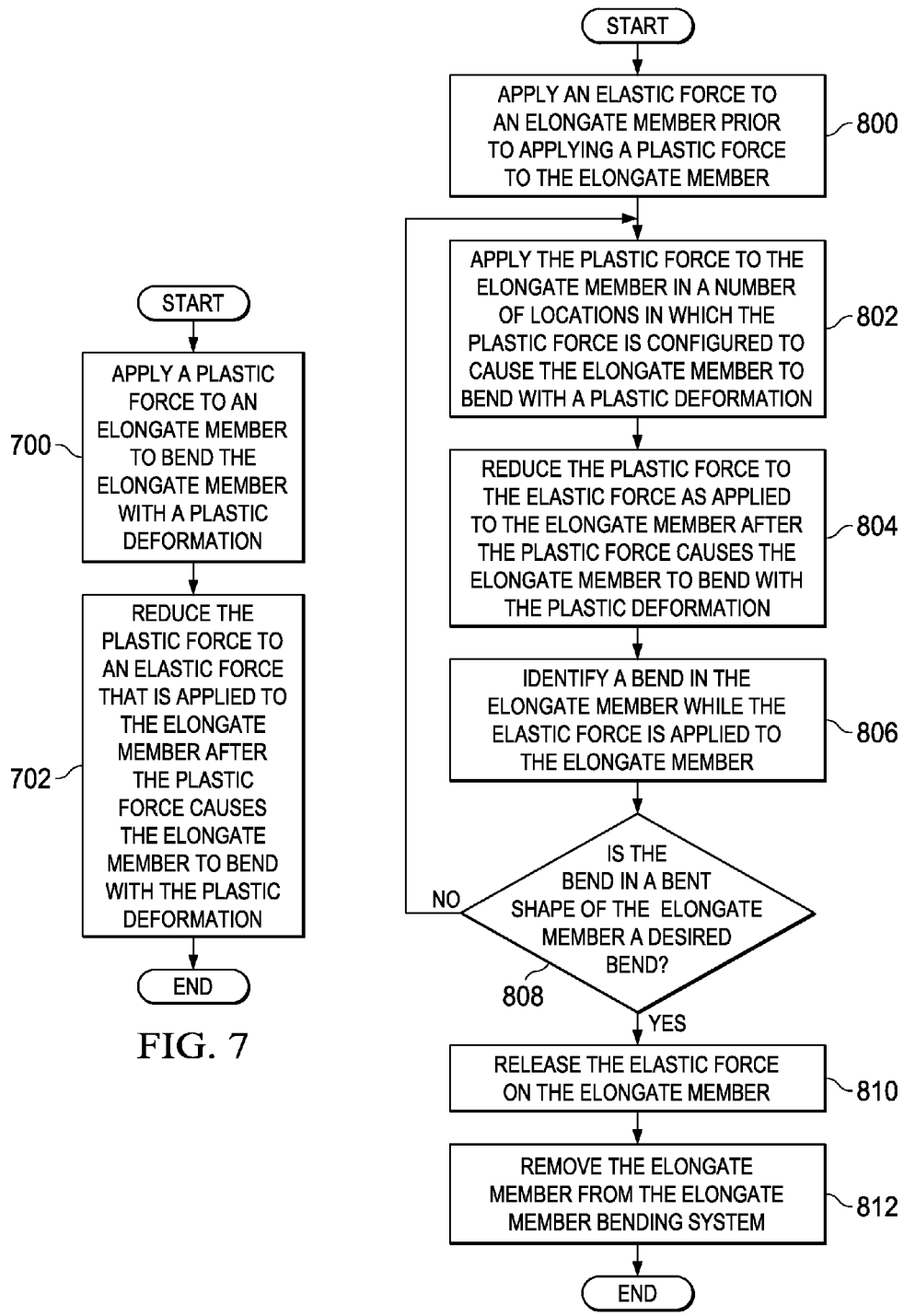

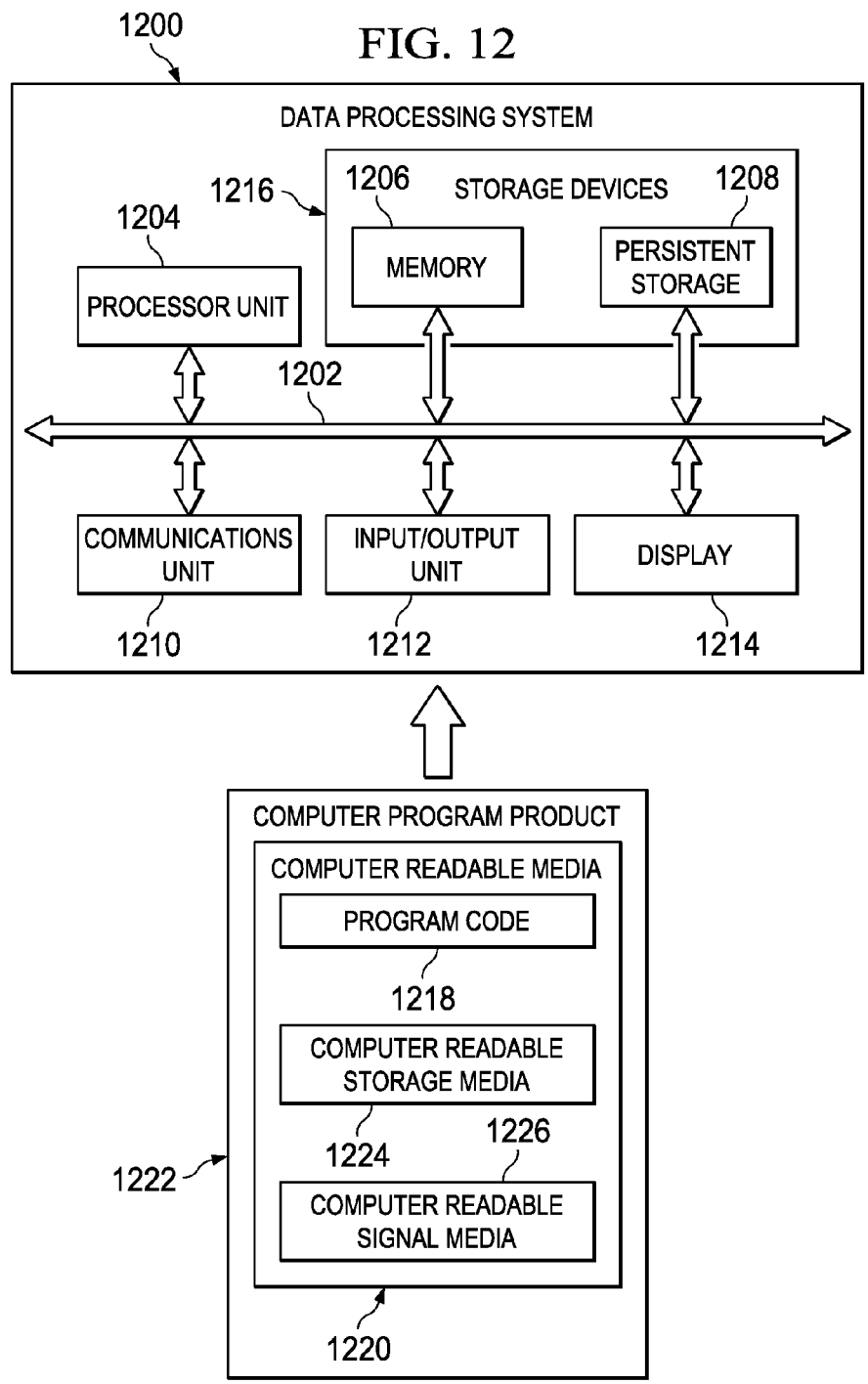

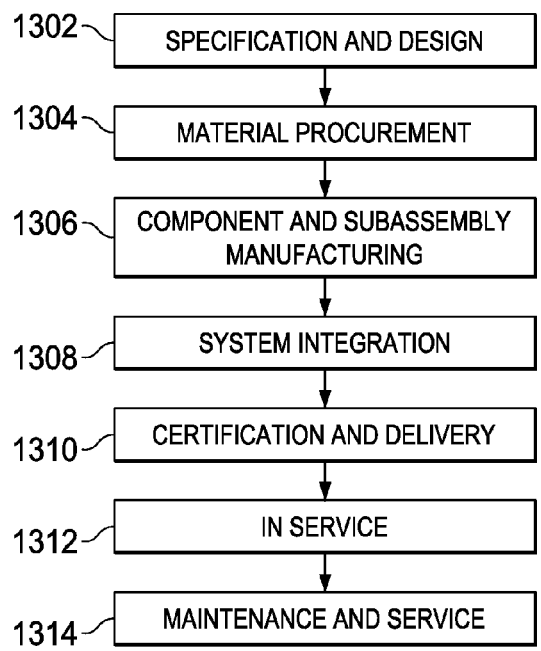
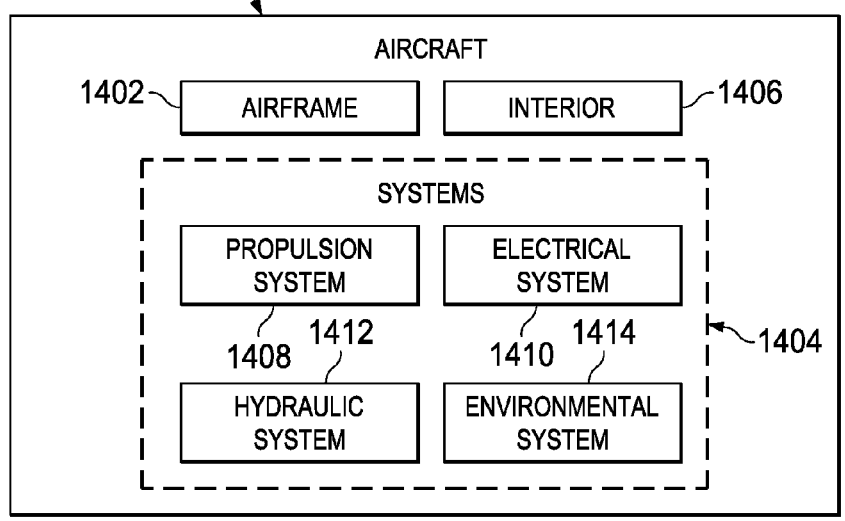

DYNAMIC STRINGER FORMING SYSTEM

BACKGROUND INFORMATION

1. Field

The present disclosure relates generally to manufacturing and, in particular, to manufacturing parts for aircraft. Still more particularly, the present disclosure relates to a method and apparatus for forming elongate members for an aircraft.

2. Background

With an aircraft, hundreds of thousands of parts may be manufactured and assembled to form the aircraft. For example, a wing of an aircraft may be formed from a wing box that may be associated with the fuselage of the aircraft. The wing box may extend from the root of the wing to the tip of the wing. Skin panels may be attached to the wing box to form the aerodynamic surfaces of the wing.

These skin panels also may include structural reinforcements. These structural reinforcements may include, for example, without limitation, stringers that may extend from the root of the wing to the tip of the wing. These stringers may be arranged within the wing to provide a desired structural stability and integrity for the skin panels such that operational loads may be applied to the wing.

As another example, the fuselage of the aircraft may be comprised of a truss or frame that may be covered by skin panels. The skin panels of the fuselage may be reinforced through the use of structures such as stringers. These stringers may extend along the length of the fuselage and may also extend around the circumference of the fuselage.

Aircraft stringers may be formed from different types of materials. For example, a stringer may be formed from a metal such as aluminum, titanium, or some other suitable metal. When stringers are formed of metal, the stringers may be initially formed with a straight shape. If the structure to which the stringer may be attached has a curve, the stringer may be changed in shape to conform the shape of the structure. For example, the wing, the fuselage, or both the wing and the fuselage may have curved sections of skin panels on which stringers may be located. These stringers for curved structures may be shaped to conform to the shape of the wing or fuselage on which the stringers may be placed.

A stringer may be shaped by bending the stringer with a tool. The bend formed in the stringer may have a curvature that conforms to the portion of structure that also may have a corresponding curve. Bending a stringer to have a bent shape may be more complex and time-consuming than desired.

Currently, a stringer may be bent using a tool in the form of a press. A human operator may position the stringer on the press. The operator may then apply a force to the stringer that causes the stringer to bend. Thereafter, the operator may release the force applied by the press and remove the stringer from the press.

The operator may then measure the amount of displacement in the stringer with the bent shape as compared to the original shape of the stringer. This measurement may be made using a gauge or other suitable measurement device. The displacement of the stringer may be used to identify the bend of the stringer.

If the amount of bend of the stringer is not great enough, the operator may then reposition the stringer back onto the press to increase the bend in the stringer using the press. In the same manner, the operator may use the press to apply pressure to the stringer to increase the bend in the stringer.

This process may be repeated many times until the stringer has a desired bend. Removing and replacing the stringer from the press may be undesirable.

Further, with this process, the accuracy in bending the stringer may not be as great as desired. If the stringer is bent such that the curvature of the bend is greater than desired, the stringer may need to be reworked to reduce the bend. Reworking the stringer to reduce the curvature of the bend may take additional time that may be greater than desired. In some cases, the bend in the stringer may be such that the stringer cannot be reworked. As a result, the stringer may be discarded and a new stringer may be processed. Consequently, the output in manufacturing stringers may be slower and more costly than desired.

Inexperienced operators may take even longer periods of time to form a stringer than experienced operators. As a result, if experienced operators are unavailable, even fewer stringers may be manufactured than desired in a given period of time.

Therefore, it would be desirable to have a method and apparatus that takes into account at least some of the issues discussed above, as well as other possible issues.

SUMMARY

In one illustrative embodiment, a method for bending an elongate member may be present. A plastic force may be applied to the elongate member. The plastic force may be configured to cause the elongate member to bend with a plastic deformation. The plastic force may be reduced to an elastic force that is applied to the elongate member after the plastic force causes the elongate member to bend with the plastic deformation.

In another illustrative embodiment, a method for dynamically forming a bend in an elongate member may be present. A force configured to cause plastic deformation in the elongate member may be applied to form the bend. The force applied to the elongate member may be reduced to cause elastic deformation in the elongate member.

In yet another illustrative embodiment, an apparatus may comprise an elongate member bending system. The elongate member bending system may be configured to apply a plastic force to an elongate member. The plastic force may be configured to cause the elongate member to bend with a plastic deformation. The elongate member bending system may be further configured to reduce the plastic force to an elastic force that is applied to the elongate member after the plastic force causes the elongate member to bend with the plastic deformation.

In still another illustrative embodiment, a method for bending a stringer for an aircraft may be present. An elastic force may be applied to an elongate member prior to applying a plastic force to the elongate member. A bend of the elongate member may be identified while the elastic force is applied to the elongate member prior to applying the plastic force. The plastic force may be applied to the elongate member. The plastic force may be configured to cause the elongate member to bend with a plastic deformation. The plastic force may be reduced to the elastic force that is applied to the elongate member after the plastic force causes the elongate member to bend with the plastic deformation. The plastic force and the elastic force may be applied in a number of locations on the elongate member. The steps of applying the elastic force to the elongate member prior to applying the plastic force to the elongate member, identifying the bend of the elongate member while the elastic force is applied to the elongate member prior to applying the plastic force, and applying the plastic force to the elongate member in which the plastic force may be configured to cause the elongate member to bend with the plastic deformation may be repeated until the bend of the elongate member is a desired bend for the elongate member.

In a further illustrative embodiment, a method for dynamically forming a bend in an elongate member may be present. A force configured to cause plastic deformation in the elongate member may be applied to form the bend. The force applied to the elongate member may be reduced to cause elastic deformation in the elongate member. The bend may be measured. A determination may be made be made as to whether the bend in the elongate member is a desired bend. The applying, reducing, and measuring steps may be repeated until the bend in the elongate member is the desired bend.

In still yet another illustrative embodiment, an apparatus may comprise an elongate member bending system. The elongate member bending system may be configured to apply an elastic force to an elongate member prior to applying a plastic force to the elongate member. The elongate member bending system may be further configured to identify a bend of the elongate member while the elastic force is applied to the elongate member prior to applying the plastic force. The elongate member bending system may be further configured to apply the plastic force to the elongate member. The plastic force may be configured to cause the elongate member to bend with a plastic deformation. The elongate member bending system may be further configured to reduce the plastic force to the elastic force that is applied to the elongate member after the plastic force causes the elongate member to bend with the plastic deformation. The plastic force and the elastic force may be applied in a number of locations on the elongate member. The elongate member bending system may comprise a press, a controller, and a measurement system. The press may be configured to apply forces on the elongate member. The controller may be configured to control the press to apply the plastic force to the elongate member. The plastic force may be configured to cause the elongate member to bend with the plastic deformation. The controller may be further configured to reduce the plastic force to the elastic force that is applied to the elongate member after the plastic force causes the elongate member to bend with the plastic deformation. The measurement system may be configured to measure the bend in the elongate member.

The features and functions can be achieved independently in various embodiments of the present disclosure or may be combined in yet other embodiments in which further details can be seen with reference to the following description and drawings.

BRIEF DESCRIPTION OF THE DRAWINGS

The novel features believed characteristic of the illustrative embodiments are set forth in the appended claims. The illustrative embodiments, however, as well as a preferred mode of use, further objectives and features thereof, will best be understood by reference to the following detailed description of an illustrative embodiment of the present disclosure when read in conjunction with the accompanying drawings, wherein:

FIG. 7 is an illustration of a flowchart of a process for bending an elongate member in accordance with an illustrative embodiment;

FIG. 8 is an illustration of a flowchart of additional processes for bending an elongate member in accordance with an illustrative embodiment;

FIG. 12 is an illustration of a block diagram of a data processing system in accordance with an illustrative embodiment;

FIG. 13 is an illustration of an aircraft manufacturing and service method in accordance with an illustrative embodiment; and FIG. 14 is an illustration of an aircraft in which an illustrative embodiment may be implemented.

DETAILED DESCRIPTION

The illustrative embodiments recognize and take into account one or more different considerations. The illustrative embodiments recognize and take into account that the current process for bending a stringer may be inefficient. As a result, the illustrative embodiments may continually apply force to the stringer during the process such that the stringer may not be removed until the stringer has a desired bend.

The stringer may not be removed in the illustrative examples to make measurements of the bend of the stringer in real time. In other words, the illustrative embodiments may measure the bend of the stringer without mechanical measurement by a human operator. This process may result in faster, more accurate, and cost efficient manufacturing of stringers for aircraft.

For example, in one illustrative embodiment, a method and apparatus for bending an elongate member may be used. A plastic force may be applied to the elongate member such that the plastic force may be configured to cause the elongate member to bend with plastic deformation. The plastic force may be reduced to an elastic force and applied to the elongate member after the plastic force.

A measurement of the bend in the elongate member may be made while the elastic force may be applied to the elongate member. As necessary to obtain a desired bend in the elongate member, the plastic force may be reapplied to increase the bend in the elongate member. In this manner, incremental increases in the bend of the elongate member may be made until the elongate member has the desired bend.

Figure 1:
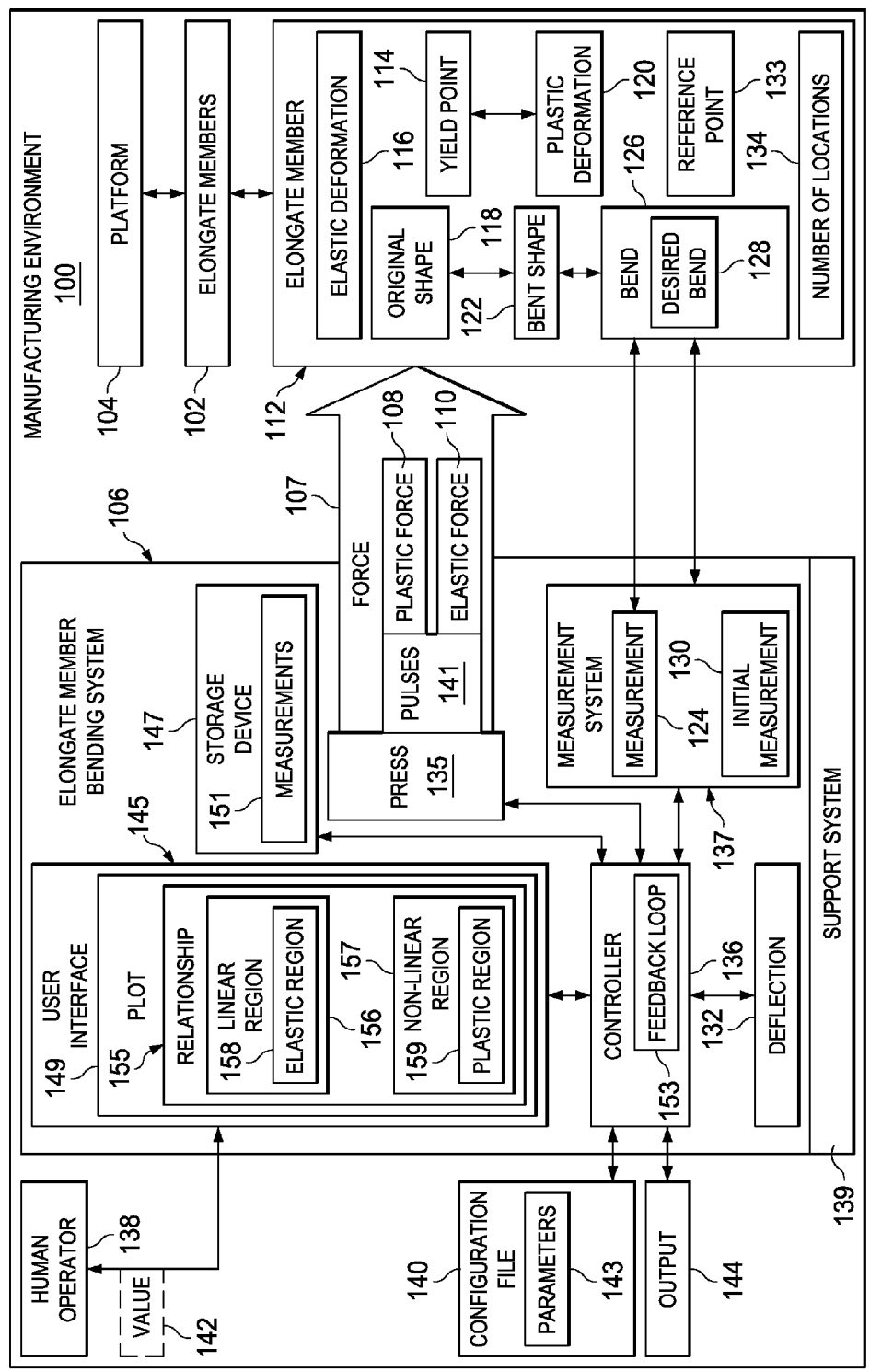
FIG. 1 is an illustration of a block diagram of a manufacturing environment in accordance with an illustrative embodiment.

With reference now to the figures and, in particular, with reference to FIG. 1, an illustration of a block diagram of a manufacturing environment is depicted in accordance with an illustrative embodiment. In this illustrative example, manufacturing environment 100 may be used to bend elongate members 102 for use in platform 104.

In these illustrative examples, platform 104 may take various forms. Platform 104 may be, for example, without limitation, a mobile platform, a stationary platform, a land-based structure, an aquatic-based structure, and a space-based structure. More specifically, the platform may be an aircraft, a surface ship, a tank, a personnel carrier, a train, a spacecraft, a space station, a satellite, a submarine, an automobile, a power plant, a bridge, a dam, a house, a manufacturing facility, a building, and other suitable objects.

In these illustrative examples, elongate members 102 may take a number of different forms. For example, without limitation, an elongate member in elongate members 102 may be selected from one of a stringer, a spar, a beam, and other suitable types of elongate members. In these illustrative examples, elongate members 102 may be comprised of any material that may bend. In particular, materials for elongate members 102 may be comprised of a metal, metal alloy, steel, titanium, aluminum, an aluminum alloy, and other suitable materials. For example, without limitation, elongate members may be metal stringers.

In this illustrative example, manufacturing environment 100 may include elongate member bending system 106. Elongate member bending system 106 may be configured to bend elongate members 102.

As depicted, elongate member bending system 106 may be configured to apply force 107 in the form of at least one of plastic force 108 and elastic force 110 to elongate member 112 in elongate members 102. As used herein, the phrase "at least one of," when used with a list of items, means different combinations of one or more of the listed items may be used and only one of each item in the list may be needed. For example, "at least one of item A, item B, and item C" may include, without limitation, item A or item A and item B. This example also may include item A, item B, and item C or item B and item C.

The illustrative embodiments recognize and take into account that an elongate member, such as elongate member 112, may have yield point 114. Yield point 114 may be an amount of force 107 at which elongate member 112 begins to deform plastically instead of elastically. Yield point 114 may be measured as stress. This stress may be the expressed as an amount of force 107 over a particular area.

In this illustrative example, plastic force 108 may cause plastic deformation 120 of elongate member 112 that may be nonreversible. In other words, when elongate member 112 bends with plastic deformation 120, elongate member 112 may not return to original shape 118. For example, without limitation, elongate member 112 may bend when plastic force 108 is applied to elongate member 112. This bend may be a desired deformation for elongate member 112.

As depicted, plastic force 108 may be an external force applied to elongate member 112 by elongate member bending system 106. For example, without limitation, plastic force 108 may be applied on elongate member 112 by a hydraulic system, a pneumatic system, a press, a ram, or some other suitable type of system.

Elastic force 110 may be a force that allows elongate member 112 to return to original shape 118. In other words, elastic force 110 may cause elongate member 112 to bend while elastic force 110 is applied to elongate member 112. This bend may be elastic deformation 116 in elongate member 112. When elastic force 110 is removed from elongate member 112, elongate member 112 may return to original shape 118. Conversely, release of plastic force 108 may not return elongate member 112 to original shape 118. Elastic force 110 also may be an external force applied to elongate member 112 by elongate member bending system 106.

In these illustrative examples, elongate member bending system 106 may be configured to apply elastic force 110 to elongate member 112. Elastic force 110 for elongate member 112 may be selected based on at least one of the properties of the material for elongate member 112, the length of elongate member 112, or some other suitable parameter.

After elastic force 110 is applied to elongate member 112, elongate member bending system 106 may apply plastic force 108 to elongate member 112 such that elongate member 112 bends with plastic deformation 120. In other words, if plastic force 108 is removed, elongate member 112 may not return to original shape 118. Instead, elongate member 112 may have bent shape 122.

After plastic force 108 is applied such that elongate member 112 bends to have bent shape 122, plastic force 108 applied to elongate member 112 may be reduced to elastic force 110 applied to elongate member 112. Elastic force 110 may be the amount as when elastic force 110 was originally applied to elongate member 112.

With the reduction of plastic force 108 to elastic force 110, elongate member 112 may remain in bent shape 122 as applied by plastic force 108. In other words, the reduction of force 107 from plastic force 108 to elastic force 110 may not result in a further deformation of elongate member 112. Measurement 124 may be made of plastic deformation 120 relative to elastic deformation 116.

Specifically, measurement 124 may be made of bend 126 of elongate member 112 with bent shape 122. Measurement 124 of bend 126 of bent shape 122 of elongate member 112 may be made without removing elongate member 112 from elongate member bending system 106. Measurement 124 of bend 126 may be made while elastic force 110 continues to be applied to elongate member 112.

In this example, if bend 126 is not desired bend 128, elastic force 110 may be increased to plastic force 108. Plastic force 108 may further bend elongate member 112 to increase bend 126 in elongate member 112. Plastic force 108 may then be reduced to elastic force 110 and measurement 124 may again be made to identify bend 126 of elongate member 112 in bent shape 122.

In these illustrative examples, the application of plastic force 108 to bend elongate member 112 and measurement 124 of elongate member 112 after bending of elongate member 112 while elastic force 110 is applied may be repeated until elongate member 112 has desired bend 128 in bent shape 122. In this manner, bend 126 may be increased incrementally until desired bend 128 is reached in bent shape 122 for elongate member 112.

This incremental increase in bend 126 of bent shape 122 of elongate member 112 may result in more accurate bending of elongate member 112. As a result, manufacturing of elongate members 102 may be performed more efficiently and with less rework that currently used systems for bending elongate members 102.

Additionally, initial measurement 130 of bend 126 of elongate member 112 also may be made while elastic force 110 is applied to elongate member 112 prior to elongate member 112 being bent with plastic force 108. In other illustrative examples, initial measurement 130 may be made prior to elastic force 110 being applied to elongate member 112.

Initial measurement 130 may be a reference measurement for measurement 124 such that deflection 132 in elongate member 112 may be identified. With deflection 132, elongate member bending system 106 may identify bend 126 and may determine whether bend 126 is desired bend 128 based on deflection 132. In these illustrative examples, deflection 132 may be desired bend 128 based on a curvature of an aircraft structure in which elongate member 112 may be located.

In these illustrative examples, plastic force 108 and elastic force 110 may be applied to number of locations 134 on elongate member 112. A "number of" as used herein with reference to items means one or more items. For example, number of locations 134 may be one or more locations on elongate member 112.

As depicted, elongate member bending system 106 may include a number of different components. For example, elongate member bending system 106 may include press 135, controller 136, and measurement system 137.

In these illustrative examples, press 135 may be a tool configured to change the shape of a workpiece, such as elongate member 112. Press 135 may be configured to apply plastic force 108 and elastic force 110 to elongate member 112. Additionally, press 135 may include support system 139. Support system 139 may be configured to hold elongate member 112 while at least one of plastic force 108 and elastic force 110 are applied to elongate member 112.

In these illustrative examples, press 135 may take various forms. For example, press 135 may be selected from at least one of a hydraulic press, a pneumatic press, a mechanical press, or some other suitable type of system configured to bend elongate member 112.

Measurement system 137 may be configured to identify bend 126 in elongate member 112. In particular, measurement system 137 may measure bend 126 in elongate member 112 after force 107 applied by press 135 has been reduced from plastic force 108 elastic force 110.

In these illustrative examples, measurement system 137 may be implemented using a number of different types of measurement systems. For example, measurement system 137 may include at least one of a laser measurement system, a camera measurement system, an ultrasonic measurement system, and other suitable types of measurement systems. Measurement system 137 may measure bend 126 continuously as elastic force 108 and/or plastic force 110 are applied to elongate member 112.

Each measurement 124 made by measurement system 137 may be stored in storage device 147 to form measurements 151. Storage device 147 may be configured store measurements 151 for use by controller 136 to plot measurements 151 in plot 149.

Measurements 151 stored in storage device 147 also may be used as a reference for future operation of elongate member bending system 106 with the same type of material. As a result, storing measurements 151 in storage device 147 may aid in efficient bending of elongate member 112 by decreasing the number of iterations required to reach desired bend 128. In other words, with measurements 151 stored in storage device 147, controller 136 may apply the appropriate level of plastic force 108 to reach desired bend 128 in elongate member 112 more efficiently using measurements 151.

In this illustrative example, plot 149 may be a graphical representation of force 107 applied to elongate member 112 in relation to deflection 132 in elongate member 112. In other words, plot 149 may represent deflection 132 of elongate member 112 at different amounts of force 107 applied to elongate member 112 by press 135 in elongate member bending system 106.

As depicted, plot 149 may be displayed to human operator 138 through user interface 145. User interface 145 may be configured to display information and/or may be used to input information by human operator 138. With the display of plot 149 on user interface 145, human operator 138 may view a graphical representation of force 107 relative to deflection 132 in substantially real-time.

For example, when elastic force 110 is applied to elongate member 112, plot 149 may show relationship 155 between force 107 and deflection 132. Linear region 156 in plot 149 may indicate elastic force 108 may be present. Linear region 156 may be elastic region 158 of elongate member 112 in these illustrative examples. Elastic region 158 may be a portion of a number of elastic regions for elongate member 112 in these illustrative examples.

When non-linear region 157 is reached in plot 149, force 107 may have reached yield point 114. Non-linear region 157 of plot 149 may indicate that force 107 has reached plastic force 108 and plastic deformation 120 of elongate member 112 may have occurred. Non-linear region 157 may be plastic region 159 in these illustrative examples. Plastic region 159 may be a portion of a number of plastic regions in this example.

In other illustrative examples, measurement system 137 may measure reference point 133 on elongate member 112 before elastic force 110 or plastic force 108 is applied to elongate member 112. Reference point 133 may be a point on elongate member 112 where measurement 124 is taken.

Further, in some illustrative examples, measurement system 137 may continuously measure bend 126 in elongate member 112. In other words, measurement system 137 may measure bend 126 in elongate member 112 while plastic force 108 is applied to elongate member 112 and while elastic force 110 is applied to elongate member 112. In this manner, measurement system 137 may measure the incremental changes in bend 126 of bent shape 122 in elongate member 112.

Additionally, these incremental changes in bend 126 of bent shape 122 in elongate member 112 may be measured by measurement system 137 while elastic force 108 is applied to elongate member 112. In this illustrative example, plastic force 108 may be applied to elongate member 112 and plastic deformation 120 may have occurred. Press 135 may decrease force 107 from plastic force 108 to elastic force 110. Elastic force 110 may remain on elongate member 112 throughout the measurement process. Deflection 132 may be measured and stored in storage device 147 for use by controller 136 in generating plot 149. In this manner, measurement 124 of incremental changes in deflection 132 may allow for the calculation of bend 126 without unclamping elongate member 112 from elongate member bending system 106.

Further, with the use of elongate member bending system 106 in this manner, knowing the material properties of elongate member 112 may not be necessary. For example, controller 136 may calculate how much press 135 is moving relative to the decrease in force 107 as applied by press 135 to elongate member 112. From this calculation, controller 136 may plot force 107 relative to the change in position of press 135 in plot 149 and calculate the amount of bend 126 that was achieved in this iteration. As a result, the material properties of elongate member 112 are not needed to determine the amount of bend 126 in elongate member 112.

Instead, the change in deflection 132 from the plastic region 159 to the elastic region 158 of elongate member 112 may be measured in substantially real-time and may serve as the basis for calculating bend 126. Of course, other relationships between force 107 from press 135 and bend 126 of elongate member 112 may be shown in plot 149, depending on the particular implementation.

As depicted, controller 136 may be configured to control the operation of press 135 and measurement system 137. Further, controller 136 may be configured to control press 135 to apply plastic force 108 and elastic force 110 to elongate member 112 in a series of operations such that desired bend 128 may be achieved for elongate member 112.

Controller 136 may be configured to control press 135 such that press 135 applies force 107 in pulses 141. Pulses 141 from press 135 may occur such that incremental changes in bend 126 of bent shape 122 in elongate member 112 occur quickly. As a result, desired bend 128 in elongate member 112 may be reached more quickly in these illustrative examples.

Additionally, controller 136 also may control measurement system 137 to make measurement 124 and initial measurement 130. Measurement system 137 may send measurement 124 and initial measurement 130 to controller 136 in these illustrative examples. Controller 136 may use measurement 124 and initial measurement 130 to identify deflection 132 as well as make other calculations or identifications. This information about deflection 132 may provide feedback for controller 136 to operate elongate member bending system 106.

As a result, feedback loop 153 may be implemented using controller 136 to control the application of force 107 by press 135 to elongate member 112. Feedback loop 153 may include input from human operator 138. In other instances, controller 136 may control the application of force 107 by press 135 without input from human operator 138.

For example, if deflection 132 does not result in desired bend 128, controller 136 may cause press 135 to apply plastic force 108 to increase deflection 132 in bent shape 122 of elongate member 112. After a second amount of plastic force 108 is applied to elongate member 112, elongate member 112 is returned to elastic region 158 for measurement. Measurement 124 is again made by measurement system 137 and compared to initial measurement 130 to identify deflection 132.

The process continues to provide feedback to controller 136 to operate press 135 of elongate member bending system 106 until deflection 132 results in desired bend 128. When desired bend 128 is present in elongate member 112, bending of elongate member 112 may be discontinued. In this manner, measurement system 137 provides feedback to controller 136 for operation of press 135 in a desired manner. As a result, the bending of elongate member 112 may occur more accurately and efficiently than with currently used systems for bending elongate members 102.

Moreover, controller 136 also may display information to human operator 138 and may receive input from human operator 138 to control the operation of elongate member bending system 106. For example, controller 136 may receive value 142 for desired bend 128 of elongate member 112 as input from human operator 138. Human operator 138 may input value 142 for desired bend 128 of elongate member 112 into user interface 145.

When controller 136 receives value 142, controller 136 may then control elongate member bending system 106 and measurement system 137 to incrementally change bend 126 to reach desired bend 128 in elongate member 112 as input by human operator 138 occurs. As a result, the interaction of human operation 138 with elongate member bending system 106, elongate member 112, or both may be reduced.

As depicted, controller 136 may be implemented in a number of different ways. For example, controller 136 may take the form of a computer system, an integrated circuit, a program in press 135, or in some other form depending on the particular implementation.

In this manner, human operator 138 may operate elongate member bending system 106 in a manner such that human operator 138 may avoid removing elongate member 112 to make measurements of bend 126 of elongate member 112. Further, human operator 138 may select configuration file 140 for elongate member 112 as input to controller 136 such that press 135 applies plastic force 108 in a manner that does not cause elongate member 112 to have bend 126 that is greater than desired bend 128.

Instead, bend 126 may be increased incrementally by press 135 under the control of controller 136 until bend 126 reaches desired bend 128. The amount of increase in bend 126 may reduce as bend 126 approaches desired bend 128. This operation of elongate member bending system 106 may be performed automatically by controller 136. As depicted, the incremental increase may reduce in size as bend 126 approaches desired bend 128.

In these illustrative examples, configuration file 140 may set out parameters for operating press 135 to generate bend 126 in elongate member 112 with desired bend 128. Parameters 143 in configuration file 140 may include at least one of a level of the elastic force, a level of the plastic force, a value for desired bend 128, the frequency for pulses 141 of press 135, or some other suitable parameters. In other illustrative examples, human operator 138 may manually input values for these parameters into controller 136.

Thus, in these illustrative examples, force 107 in the form of at least one of plastic force 108 and elastic force 110 is applied to elongate member 112 until elongate member 112 has desired bend 128. As a result, a constant force may remain applied to elongate member 112 in the form of elastic force 110, plastic force 108, or both elastic force 110 and plastic force 108. In this manner, elongate member bending system 106 may be more accurate than currently used methods which may include bending elongate member 112 from original shape 118, removing elongate member 112 from press 135, and measuring elongate member 112.

With use of the illustrative embodiments, desired bend 128 in elongate member 112 may be reached more quickly and accurately by measuring small changes in bend 126 using measurement system 137. Continuous measurement of deflection 132 in elongate member 112 reduces the amount of error in over-bending that may occur in elongate member 112.

Further, with the use of an illustrative embodiment, the elastic characteristics of elongate member 112 are used to determine how much elongate member 112 is bent. Thus, it is possible to determine a desired amount of plastic force 108 to be applied to elongate member 112, bend 126 of elongate member 112, or both without knowing the material properties of elongate member 112.

In other illustrative examples, controller 136 also may record at least one of the level of plastic force 108, the level of elastic force 110, deflection 132, and other suitable parameters used when bending elongate member 112 in storage device 147. This information also may be recorded as output 144. Output 144 may be used to build a configuration file, such as configuration file 140, in these illustrative examples.

Further, with use of the illustrative embodiments, removal, repositioning, and/or replacement of elongate member 112 while bending elongate member 112 to have desired bend 128 may be reduced or avoided. By avoiding the removal, repositioning, and/or replacement of elongate member 112 from press 135 after measurement 124 of elongate member 112, undesired bending of elongate member 112 that may occur when removing, repositioning, and/or replacing elongate member 112 on press 135 may be avoided.

In these illustrative examples, once elongate member 112 has desired bend 128, elongate member 112 may no longer have plastic force 108 or elastic force 110 applied to elongate member 112. In other words, an absence of force 107 may be present on elongate member 112. Measurement system 137 may make a final measurement of bend 126. Additionally, human operator 138 also may verify that bend 126 is desired bend 128 through another measurement system. This measurement system used by human operator 138 to verify the value for desired bend 128 in elongate member 112 may be a gauge system or some other suitable type of measurement system.

The illustration of manufacturing environment 100 in FIG. 1 is not meant to imply physical or architectural limitations to the manner in which an illustrative embodiment may be implemented. Other components in addition to or in place of the ones illustrated may be used. Some components may be unnecessary. Also, the blocks are presented to illustrate some functional components. One or more of these blocks may be combined, divided, or combined and divided into different blocks when implemented in an illustrative embodiment.

For example, in some illustrative examples, one or more additional bends in addition to bend 126 may be formed in elongate member 112. These bends may be formed using elongate member bending system 106. In this case, once desired bend 128 for a first bend in elongate member 112 is reached, elongate member 112 may be moved such that support system 139 may secure elongate member 112 at a different section of elongate member 112. Controller 136 may then control press 135 and measurement system 137 such that desired bend 128 results at a second bend in elongate member 112.

In yet another illustrative example, if additional bends are to be formed in elongate member 112 in addition to bend 126, one or more additional presses may be used in addition to press 135 or press 135 may be configured to form multiple bends within elongate member 112. Movement of elongate member 112, press 135, multiple presses similar to press 135 in elongate member bending system 106, or a combination thereof may occur automatically or by human operator 138.

Figure 2:
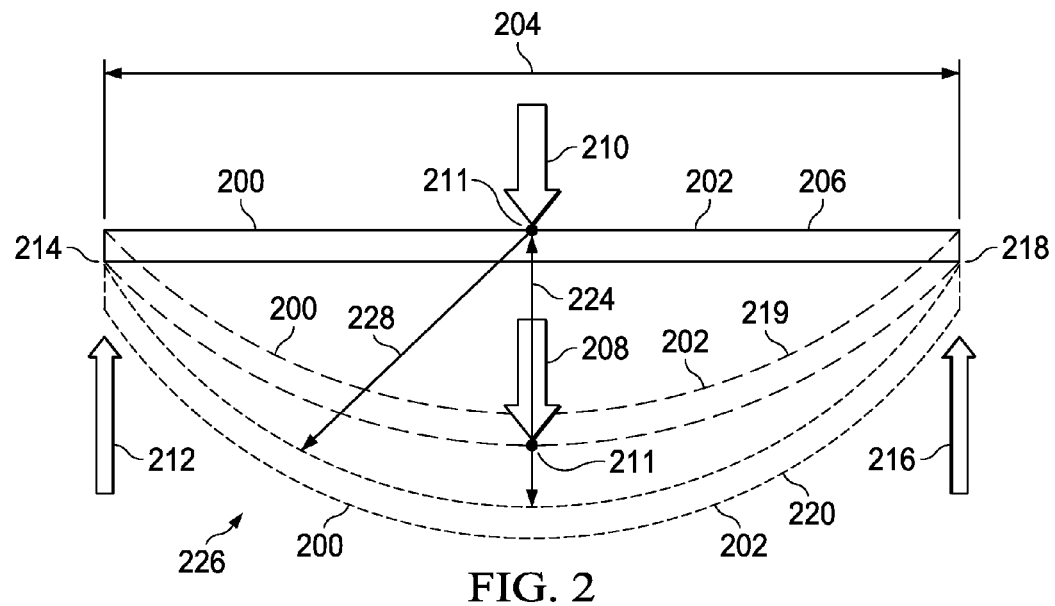
FIG. 2 is an illustration of bending of an elongate member in accordance with an illustrative embodiment.

With reference now to FIG. 2, an illustration of bending of an elongate member is depicted in accordance with an illustrative embodiment. Elongate member 200 may be an example of one physical implementation for elongate member 112 shown in block form in FIG. 1.

In this depicted example, elongate member 200 may take the form of stringer 202. As depicted, elongate member 200 may have length 204. Elongate member 200 may have original shape 206.

In these illustrative examples, elastic force 210 may be applied to elongate member 200 at location 211. When elastic force 210 is applied to elongate member 200, original shape 206 may bend to form first bent shape 219. First bent shape 219 may be a result of elastic deformation 116 in FIG. 1 and may be reversible in these illustrative examples. As a result of elastic force 210 being applied to elongate member 200 at location 211, reactive force 212 may occur at location 214 and reactive force 216 may occur at location 218.

Thereafter, plastic force 208 may be applied to elongate member 200 at location 211. Reactive force 212 at location 214 and reactive force 216 at location 218 may increase with the application of plastic force 208 to elongate member 200.

With the application of plastic force 208 to location 211 on elongate member 200, original shape 206 may further bend to form second bent shape 220. In these illustrative examples, plastic force 208 may then be reduced to elastic force 210 and applied to location 211. With elastic force 210 applied to elongate member 200, a measurement of deflection 224 between original shape 206 and second bent shape 220 caused by plastic force 208 may be made. Deflection 224 may be used to identify bend 226 for elongate member 200 in second bent shape 220.

In a similar fashion, if bend 226 is not a desired bend for elongate member 200, plastic force 208 may be applied again and released from elongate member 200. Another measurement of deflection 224 between first bent shape 219 and second bent shape 220 may be made. If deflection 224 is a desired deflection, elastic force 210 may be released and elongate member 200 may be removed from the press. If deflection 224 is still not a desired deflection, plastic force 208 may be reapplied to elongate member 200. Subsequent measurements may be made as more force is applied to elongate member 200 until a desired bent shape is reached for elongate member 200.

In this illustrative example, the bend of elongate member 200 may be measured as radius 228. Radius 228 may be calculated from location 211. The calculation of radius 228 may be made using deflection 224. In particular, radius 228 may be calculated as follows:

$$r = c^2 + 4h^2/8h \qquad (1)$$

where r may be radius 228, c may be the fulcrum length 204 of elongate member 200, and h may be deflection 224.

When measuring deflection 224, the measurement may be extrapolated to reflect a relative zero pressure environment. This relative-zero pressure may be a pressure applied in elastic mode to elongate member 200. In other words, in order to obtain a desired accuracy for the bend of elongate member 200, the values for the bend measured when elastic force 210 is applied to elongate member 200 after plastic force 208 is applied to elongate member 200 may be extrapolated to reflect values of relative-zero pressure. As a result, the data collected from measuring the bend in elongate member 200 may represent the amount of bend in elongate member 200 when relative-zero pressure is applied to elongate member 200.

In other words, identifying the values of the bend at relative-zero pressure provides a constant reference value for comparison. Of course, one may use other values for the pressure other than zero pressure if desired.

As an example, after one iteration of applying plastic force 208 and reducing plastic force 208 to elastic force 210, deflection 224 may reflect a small bend in elongate member 200 at zero pressure. After a second iteration, deflection 224 may reflect a larger bend in elongate member 200 at relative-zero pressure. With each iteration, the amount of bend in elongate member 200 at relative-zero pressure may be compared to the desired bend for elongate member 200.

Figure 3:
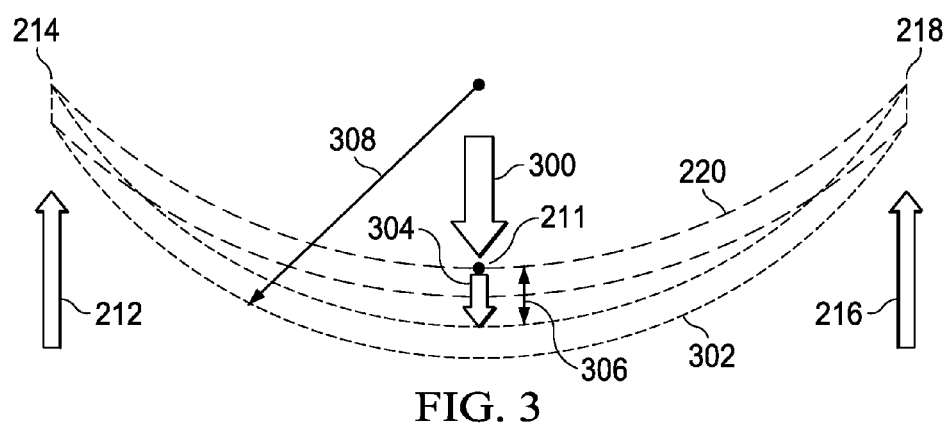
FIG. 3 is an illustration of additional bending of an elongate member in accordance with an illustrative embodiment.

Turning now to FIG. 3, an illustration of additional bending of an elongate member is depicted in accordance with an illustrative embodiment. In this example, if bend 226 in second bent shape 220 of elongate member 200 is not as great as desired, elongate member 200 may be further bent to increase bend 226 in elongate member 200. In this illustrative example, bend 226 may be measured as radius 228 which may be identified from deflection 224 in FIG. 2.

When bend 226 of elongate member 200 in second bent shape 220 does not have a desired bend, elastic force 210 may be increased to plastic force 300 at location 211. Plastic force 300 may have the same level of force as plastic force 208 or may be at some other level of force. For example, plastic force 300 may be greater than plastic force 208 in FIG. 2 in these illustrative examples.

The application of plastic force 300 may cause elongate member 200 in second bent shape 220 to further bend to third bent shape 302. Plastic force 300 may then be reduced to elastic force 304. Elastic force 304 may have the same level of force as elastic force 210 in FIG. 2, or may have a different level of force depending on the particular implementation.

While elastic force 304 is applied to location 211, a measurement of deflection 306 may be made. Deflection 306 may be the distance between second bent shape 220 and third bent shape 302 at location 211. Deflection 306 may then be used with deflection 224 in FIG. 2 to identify radius 308 for third bent shape 302 of elongate member 200.

If third bent shape 302 for elongate member 200 is a desired bent shape, then the bending of elongate member 200 may be completed. Otherwise, the process of applying plastic and elastic forces to elongate member 200 may continue until a desired bend is present in elongate member 200.

In these illustrative examples, the elastic forces and plastic forces may be measured in a number of different ways. For example, these forces may be measured as stress on elongate member 200 with a measurement system such as measurement system 137 in FIG. 1.

Figure 4:
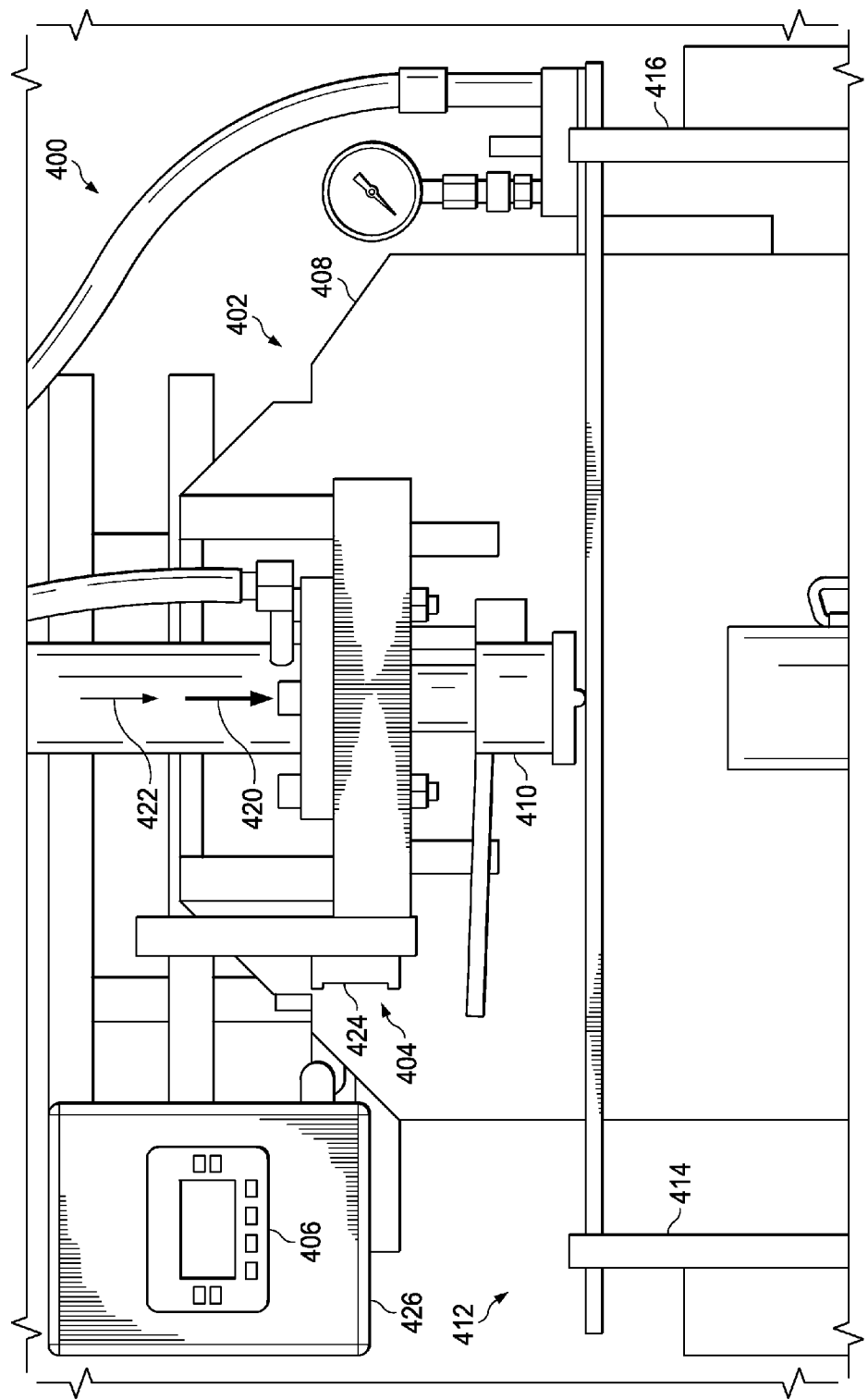
FIG. 4 is an illustration of an elongate member bending system with an elongate member in accordance with an illustrative embodiment.

With reference next to FIG. 4, an illustration of an elongate member bending system with an elongate member is depicted in accordance with an illustrative embodiment. Elongate member bending system 400 may be an example of one physical implementation for elongate member bending system 106 shown in block form in FIG. 1.

As depicted, elongate member bending system 400 may include a number of different components. For example, elongate member bending system 400 may include press 402, measurement system 404, and controller 406.

In this illustrative example, press 402 takes the form of hydraulic press 408. As depicted, hydraulic press 408 may have piston 410. Additionally, press 402 may include support system 412. Support system 412 may include support 414 and support 416. Support 414 and support 416 may be configured to lock an elongate member into place in elongate member bending system 400.

As depicted, piston 410 may be operated to generate force 420. Force 420 may be a plastic force, an elastic force, or some combination thereof. The generation of force 420 by piston 410 may occur through the movement of piston 410 in the direction of arrow 422.

In this illustrative example, measurement system 404 may be associated with hydraulic press 408. As depicted, measurement system 404 may take the form of laser measurement system 424 in this illustrative example. Laser measurement system 424 may measure distances to a workpiece (not shown) held on support system 412.

As depicted, controller 406 may be associated with press 402. Controller 406 may take the form of computer 426. In this illustrative example, computer 426 may run software to control hydraulic press 408.

Of course, elongate member bending system 400 may also include other components not described in this figure that may be used in the operation of elongate member bending system 400. For example, elongate member bending system 400 may include a power supply, a pressure gauge, and other components.

Figure 5:
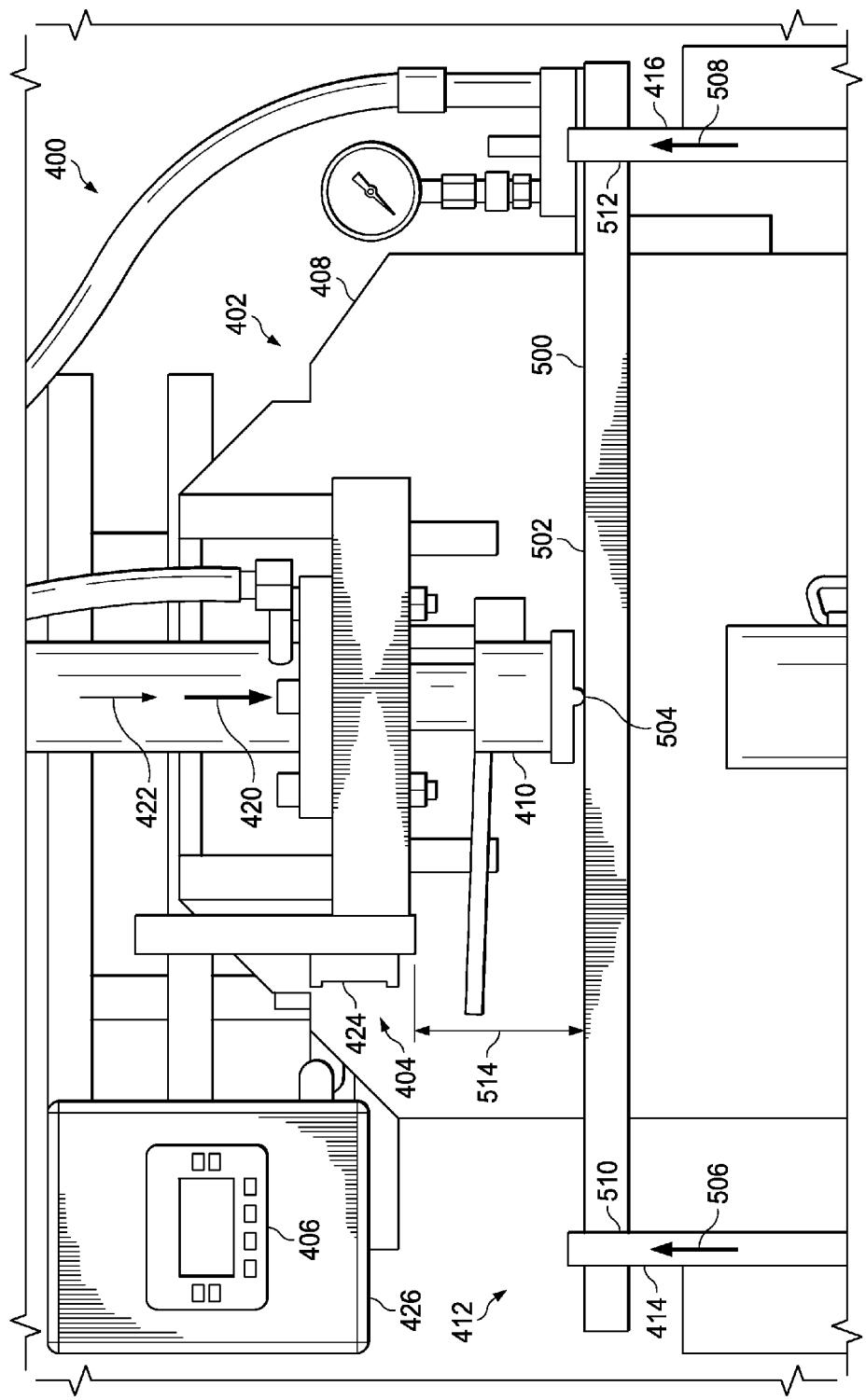
FIG. 5 is an illustration of bending of an elongate member on an elongate member bending system in accordance with an illustrative embodiment.

Turning now to FIG. 5, an illustration of bending of an elongate member on an elongate member bending system is depicted in accordance with an illustrative embodiment. In this illustrative example, elongate member 500 may take the form of stringer 502. Stringer 502 is depicted as mounted on support system 412 in hydraulic press 408.

As depicted, piston 410 may apply force 420 at location 504 on stringer 502. In response to force 420 applied to location 504, reactive force 506 and reactive force 508 may be applied to stringer 502 at location 510 and location 512, respectively. Location 510 corresponds to support 414 and location 512 corresponds to support 416.

In this illustrative example, force 420 may take the form of an elastic force. While force 420 is being applied, laser measurement system 424 may measure distance 514 from laser measurement system 424 to stringer 502. Laser measurement system 424 may measure to location 504 using distance 514 with the offset of light reflected to a detector in laser measurement system 424. More than one laser measurement system may be used to measure other locations along elongate member 500.

Figure 6:
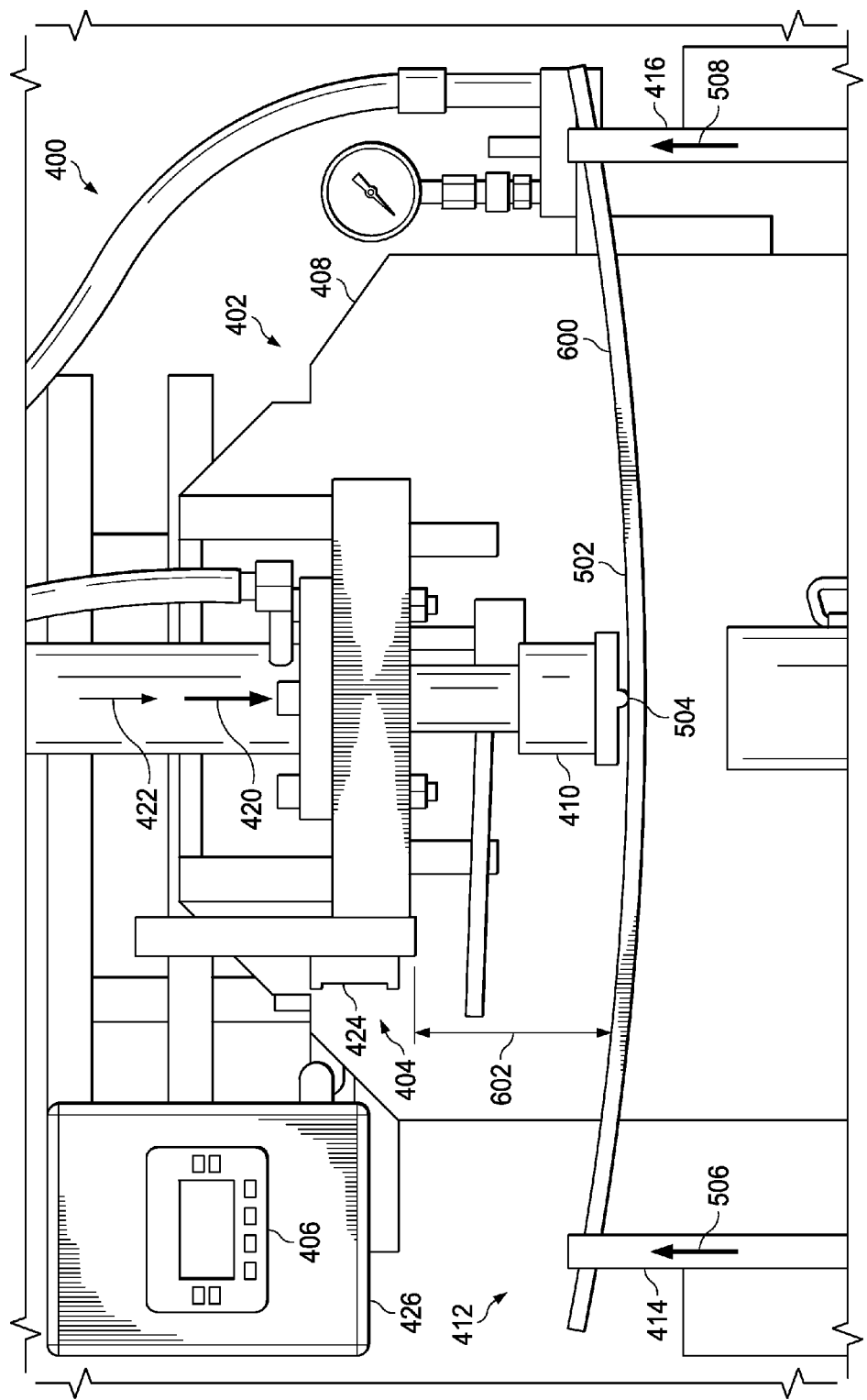
FIG. 6 is an illustration of an elongate member bending system with an elongate member in a bent shape in accordance with an illustrative embodiment.

With reference now to FIG. 6, an illustration of an elongate member bending system with an elongate member in a bent shape is depicted in accordance with an illustrative embodiment. In this example, piston 410 in hydraulic press 408 may have applied force 420 on stringer 502 in the direction of arrow 422. The force applied may be a plastic force in this illustrative example. As a result, stringer 502 may be bent and may have bent shape 600.

Thereafter, force 420 may be reduced from a plastic force to an elastic force. At this point, laser measurement system 424 may measure distance 602 to stringer 502. The difference between distance 514 in FIG. 5 and distance 602 may form a deflection that may be used by controller 406 to identify the bend of stringer 502. In particular, a radius for stringer 502 may be identified by controller 406.

If bent shape 600 does not have a desired bend, the elastic force may be increased to a plastic force to further bend stringer 502. Thereafter, the plastic force may be reduced to an elastic force and another measurement may be made of bent shape 600 for stringer 502. This process may be repeated until bent shape 600 has a desired bend for stringer 502.

The illustrations of elongate member bending system 400 in FIGS. 4-6 are not meant to imply limitations to the manner in which an elongate member bending system may be implemented. For example, in some illustrative examples, a camera system may be used to measure displacement of a stringer to identify the bend of the stringer. In another illustrative example, pistons or other force generation members may be used in place of support 414 and support 416 in support system 412.

The different components shown in FIGS. 2-6 may be combined with components in FIG. 1, used with components in FIG. 1, or a combination of the two. Additionally, some of the components in FIGS. 2-6 may be illustrative examples of how components shown in block form in FIG. 1 can be implemented as physical structures.

Turning now to FIG. 7, an illustration of a flowchart of a process for bending an elongate member is depicted in accordance with an illustrative embodiment. The process illustrated in FIG. 7 may be implemented in manufacturing environment 100 in FIG. 1. In particular, the process may be implemented using elongate member bending system 106 in FIG. 1.

The process may begin by applying plastic force 108 to elongate member 112 in which plastic force 108 may be configured to cause elongate member 112 to bend with plastic deformation 120 (operation 700). Next, plastic force 108 may be reduced to elastic force 110 applied to elongate member 112 after plastic force 108 causes elongate member 112 to bend with plastic deformation 120 (operation 702), with the process terminating thereafter.

Turning now to FIG. 8, an illustration of a flowchart of additional processes for bending an elongate member is depicted in accordance with an illustrative embodiment. The process illustrated in FIG. 8 is a more detailed example of operations that may be performed to bend elongate member 112 such that bend 126 for elongate member 112 may be desired bend 128 in FIG. 1.

The process may begin by applying elastic force 110 to elongate member 112 prior to applying plastic force 108 to elongate member 112 (operation 800). The level of plastic force 108 in this example may be insufficient to cause bend 126 in elongate member 112. This initial distance may be used to identify the amount of deflection in elongate member 112 later in this process.

The process may then apply plastic force 108 to elongate member 112 in number of locations 134 in which plastic force 108 may be configured to cause elongate member 112 to bend with plastic deformation 120 (operation 802). Plastic force 108 applied to elongate member 112 may be reduced to elastic force 110 as applied to elongate member 112 after plastic force 108 causes elongate member 112 to bend with plastic deformation 120 (operation 804). In this operation, elongate member 112 may now have bent shape 122.

The process may then identify bend 126 in elongate member 112 while elastic force 110 is applied to elongate member 112 (operation 806). As can been seen in these illustrative examples, force may be constantly applied to elongate member 112 and elongate member 112 may not need to be removed from elongate member bending system 106. When applying plastic force 108, press 135 may apply plastic force 108 in pulses 141 as described in FIG. 1.

Next, a determination may be made as to whether bend 126 in bent shape 122 of elongate member 112 is desired bend 128 (operation 808). If bend 126 for elongate member 112 is not desired bend 128, the process may return to operation 802 as described herein. Otherwise, elastic force 110 may be released on elongate member 112 (operation 810). Thereafter, elongate member 112 may be removed from elongate member bending system 106 (operation 812), with the process terminating thereafter.

Figure 9:
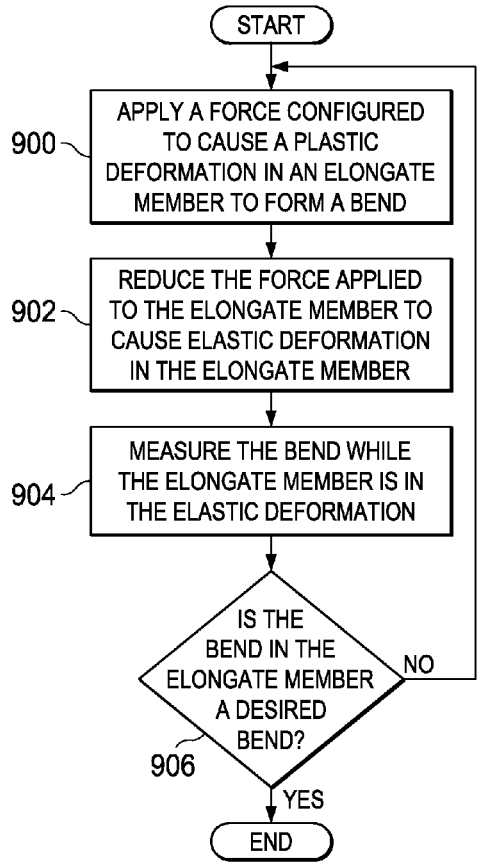
FIG. 9 is an illustration of a flowchart of a process for bending an elongate member in accordance with an illustrative embodiment.

With reference next to FIG. 9, an illustration of a flowchart of a process for bending an elongate member is depicted in accordance with an illustrative embodiment. The process illustrated in FIG. 9 may be implemented in manufacturing environment 100 in FIG. 1. In particular, the process may be implemented using elongate member bending system 106 in FIG. 1 to form desired bend 128 in elongate member 112.

The process may begin applying force 107 configured to cause plastic deformation 120 in elongate member 112 to form bend 126 (operation 900). The process may then reduce force 107 applied to elongate member 112 to cause elastic deformation 116 in elongate member 112 (operation 902).

The process may then measure bend 126 while elongate member 112 is in elastic deformation 116 (operation 904). A determination may be made as to whether bend 126 in elongate member 112 is desired bend 128 (operation 906). If bend 126 is not desired bend 128, the process may then return to operation 900. Otherwise, the process may terminate. In this manner, the different operations in FIG. 9 may form feedback loop 153 for bending elongate member 112 incrementally until desired bend 128 is reached.

Figure 10:
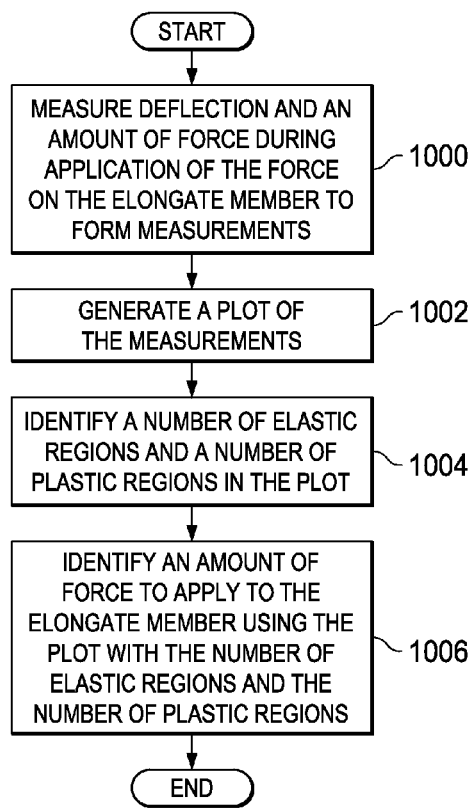
FIG. 10 is an illustration of a flowchart of a process for bending an elongate member in accordance with an illustrative embodiment.

With reference next to FIG. 10, an illustration of a flowchart of a process for bending an elongate member is depicted in accordance with an illustrative embodiment. The process illustrated in FIG. 10 may be implemented in manufacturing environment 100 in FIG. 1. In particular, the process may be implemented using elongate member bending system 106 in FIG. 1 to identify an amount of force 107 to apply to elongate member 112.

The process may begin by measuring deflection and an amount of force 107 during application of the force on the elongate member to form measurements 151 (operation 1000). Deflection 132 may be an example of the deflection. The process may then generate plot 149 of the measurements 151 (operation 1002). Number of elastic regions 158 and number of plastic regions 159 may be identified in plot 149 (operation 1004).

The process may identify an amount of force 107 to apply to elongate member 112 using plot 149 with number of elastic regions 158 and number of plastic regions 159 (operation 1006) with the process terminating thereafter. Force 107 may be identified in a number of different ways. For example, without limitation, force 107 may be identified using by at least one of human operator 138 and controller 136 in FIG. 1.

The flowcharts and block diagrams in the different depicted embodiments illustrate the architecture, functionality, and operation of some possible implementations of apparatuses and methods in an illustrative embodiment. In this regard, each block in the flowcharts or block diagrams may represent a module, a segment, a function, and/or a portion of an operation or step. For example, one or more of the blocks may be implemented as program code, in hardware, or a combination of the program code and hardware. When implemented in hardware, the hardware may, for example, take the form of integrated circuits that may be manufactured or configured to perform one or more operations in the flowcharts or block diagrams.

In some alternative implementations of an illustrative embodiment, the function or functions noted in the blocks may occur out of the order noted in the figures. For example, in some cases, two blocks shown in succession may be executed substantially concurrently, or the blocks may sometimes be performed in the reverse order, depending upon the functionality involved. Also, other blocks may be added in addition to the illustrated blocks in a flowchart or block diagram.

Figure 11:
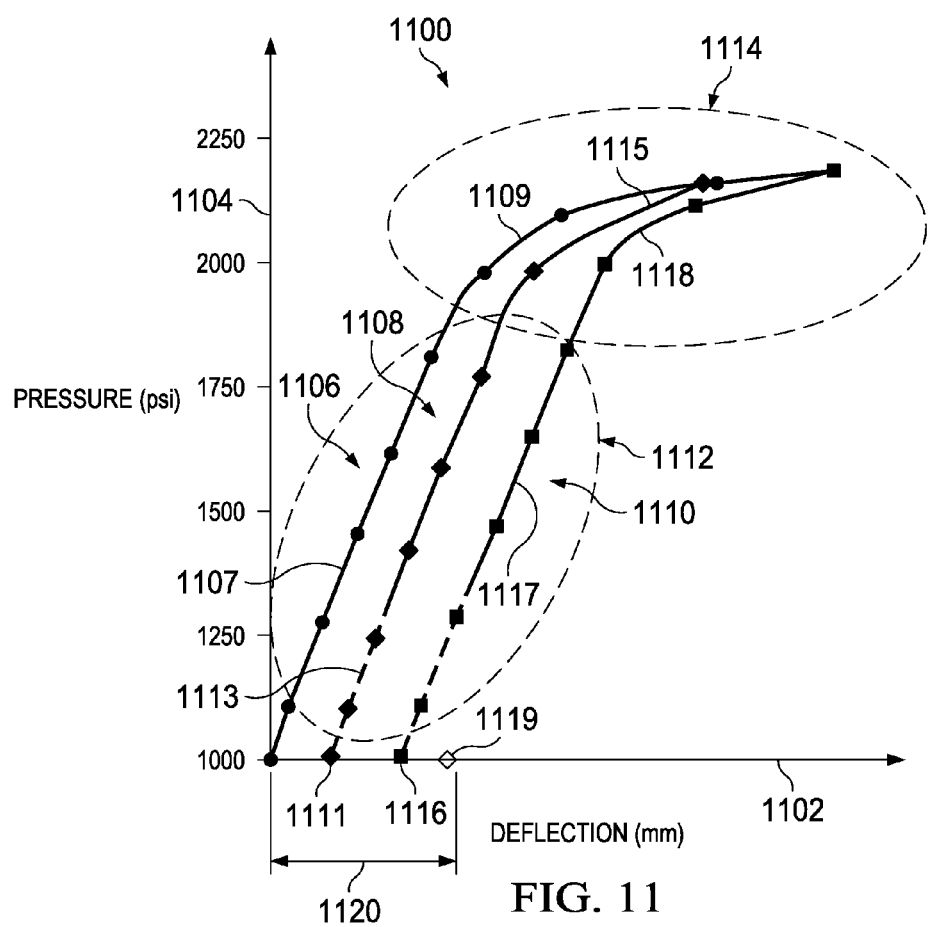
FIG. 11 is a plot with measurements in accordance with an illustrative embodiment.

With reference now to FIG. 11, a plot with measurements is depicted in accordance with an illustrative embodiment. Plot 1100 may be one example of plot 149 generated by controller 136 for display to human operator 138 on user interface 145 in FIG. 1. Plot 149 may show measurements 151 for elongate member 112 during bending of elongate member 112.

In this illustrative example, plot 1100 may have x-axis 1102 and y-axis 1104. X-axis 1102 may represent deflection 132 of elongate member 112 in FIG. 1. Deflection 132 may be measured by measurement system 137 in FIG. 1 in millimeters. Of course, other units of measurement for deflection 132 may be used, depending on the particular implementation.

Y-axis 1104 may represent pressure in these illustrative examples. The pressure in y-axis 1104 may be a measure of force 107 applied by press 135 in elongate member bending system 106 in pounds-per-square-inch (psi). Of course, other units may be used to measure force 107 from press 135, depending on the particular implementation.

In this illustrative example, force 107 may be applied to elongate member 112. Measurements 151 may be taken by measurement system 137 while force 107 is being applied to elongate member 112. Controller 136 may plot measurements 151 on line 1106 for a first iteration of movement of press 135.

In these illustrative examples, linear region 1107 of line 1106 is in elastic region 1112 of elongate member 112. In other words, a linear relationship between force 107 and deflection 132 may be present in elastic region 1112 of elongate member 112. In this case, force 107 may be elastic force 110 when in elastic region 1112.

When force 107 reaches yield point 114 in FIG. 1 for elongate member 112, plastic deformation 120 may occur. In this illustrative example, non-linear region 1109 of line 1106 may be in plastic region 1114 of elongate member 112. Plastic deformation 120 of elongate member 112 may occur in non-linear region 1109 through the application of plastic force 108 by press 135 on elongate member 112.

In these illustrative examples, force 107 may be decreased from plastic force 108 in plastic region 1114 to elastic force 110 and force 107 applied to elongate member 112 may return to elastic region 1112. The first iteration of press 135 applying force 107 on elongate member 112 may result in first deflection 1111. First deflection 1111 may or may not result in desired bend 128 of elongate member 112 in FIG. 1.

If first deflection 1111 does not result in desired bend 128 of elongate member 112, a second iteration of press 135 may be performed. During the second iteration of press 135, force 107 may be applied to elongate member 112 in elastic region 1112 and plastic region 1114. When force 107 reaches plastic force 108 in plastic region 1114, more plastic deformation 120 of elongate member 112 may occur.

Measurements 151 again may be taken during this second iteration of press 135 and may be plotted by controller 136 along line 1108. Line 1108 may have linear region 1113 and non-linear region 1115. Linear region 1113 may represent deflection 132 of elongate member 112 in elastic region 1112. Non-linear region 1115 may represent deflection 132 of elongate member 112 in plastic region 1114. Plastic force 108 may be reduced to elastic force 110.

In these illustrative examples, the second iteration of press 135 applying force 107 on elongate member 112 may result in second deflection 1116. Second deflection 1116 may or may not result in desired bend 128 in FIG. 1. If second deflection 1116 does not result in desired bend 128 of elongate member 112, a third iteration of press 135 applying force 107 to elongate member 112 may be performed.

Measurements 151 for the third iteration of press 135 may be plotted along line 1110 in these illustrative examples. Line 1110 may have linear region 1117 in elastic region 1112 and non-linear region 1118 in plastic region 1114 of elongate member 112. Force 107 may be reduced to elastic force 110.

In this case, deflection 132 measured by measurement system 137 may be desired deflection 1119. Desired deflection 1119 may result in desired bend 128 of elongate member 112. As depicted, change 1120 in deflection 132 over three iterations of press 135 applying force 107 to elongate member 112 may be seen in plot 1100. Measurements 151 in plot 1100 may be stored in storage device 147 in FIG. 1 for later use.

Although three iterations of press 135 applying force 107 to elongate member 112 are shown in this illustrative example, other numbers of iterations may be performed to reach desired deflection 1119. One iteration, five iterations, ten iterations, twenty iterations, or other numbers of iterations may be performed, depending on the particular implementation. Further, more measurements 151 may be plotted by controller 136 on plot 1100 than are shown in this illustrative example.

Turning now to FIG. 12, an illustration of a block diagram of a data processing system is depicted in accordance with an illustrative embodiment. Data processing system 1200 may be used to implement controller 136 in manufacturing environment 100 in FIG. 1, controller 406 in FIG. 4, and other suitable devices. In this illustrative example, data processing system 1200 includes communications framework 1202, which provides communications between processor unit 1204, memory 1206, persistent storage 1208, communications unit 1210, input/output unit 1212, and display 1214. In this example, communication framework may take the form of a bus system.

Processor unit 1204 serves to execute instructions for software that may be loaded into memory 1206. Processor unit 1204 may be a number of processors, a multi-processor core, or some other type of processor, depending on the particular implementation.

Memory 1206 and persistent storage 1208 may be examples of storage devices 1216. A storage device may be any piece of hardware that may be capable of storing information, such as, for example, without limitation, data, program code in functional form, and/or other suitable information either on a temporary basis and/or a permanent basis. Storage devices 1216 may also be referred to as computer readable storage devices in these illustrative examples. Memory 1206, in these examples, may be, for example, a random access memory or any other suitable volatile or non-volatile storage device. Persistent storage 1208 may take various forms, depending on the particular implementation.

For example, persistent storage 1208 may contain one or more components or devices. For example, persistent storage 1208 may be a hard drive, a flash memory, a rewritable optical disk, a rewritable magnetic tape, or some combination of the above. The media used by persistent storage 1208 also may be removable. For example, a removable hard drive may be used for persistent storage 1208.

Communications unit 1210, in these illustrative examples, provides for communications with other data processing systems or devices. In these illustrative examples, communications unit 1210 may be a network interface card.

Input/output unit 1212 allows for input and output of data with other devices that may be connected to data processing system 1200. For example, input/output unit 1212 may provide a connection for user input through a keyboard, a mouse, and/or some other suitable input device. Further, input/output unit 1212 may send output to a printer. Display 1214 provides a mechanism to display information to a user.

Instructions for the operating system, applications, and/or programs may be located in storage devices 1216, which may be in communication with processor unit 1204 through communications framework 1202. The processes of the different embodiments may be performed by processor unit 1204 using computer-implemented instructions, which may be located in a memory, such as memory 1206.

These instructions may be referred to as program code, computer usable program code, or computer readable program code that may be read and executed by a processor in processor unit 1204. The program code in the different embodiments may be embodied on different physical or computer readable storage media, such as memory 1206 or persistent storage 1208.

Program code 1218 may be located in a functional form on computer readable media 1220 that may be selectively removable and may be loaded onto or transferred to data processing system 1200 for execution by processor unit 1204. Program code 1218 and computer readable media 1220 form computer program product 1222 in these illustrative examples. In one example, computer readable media 1220 may be computer readable storage media 1224 or computer readable signal media 1226.

In these illustrative examples, computer readable storage media 1224 may be a physical or tangible storage device used to store program code 1218 rather than a medium that propagates or transmits program code 1218.

Alternatively, program code 1218 may be transferred to data processing system 1200 using computer readable signal media 1226. Computer readable signal media 1226 may be, for example, a propagated data signal containing program code 1218. For example, computer readable signal media 1226 may be an electromagnetic signal, an optical signal, and/or any other suitable type of signal. These signals may be transmitted over communications links, such as wireless communications links, optical fiber cable, coaxial cable, a wire, and/or any other suitable type of communications link.

The different components illustrated for data processing system 1200 are not meant to provide architectural limitations to the manner in which different embodiments may be implemented. The different illustrative embodiments may be implemented in a data processing system including components in addition to and/or in place of those illustrated for data processing system 1200. Other components shown in FIG. 12 can be varied from the illustrative examples shown. The different embodiments may be implemented using any hardware device or system capable of running program code 1218.

Illustrative embodiments of the disclosure may be described in the context of aircraft manufacturing and service method 1300 as shown in FIG. 13 and aircraft 1400 as shown in FIG. 14. Turning first to FIG. 13, an illustration of an aircraft manufacturing and service method is depicted in accordance with an illustrative embodiment. During pre-production, aircraft manufacturing and service method 1300 may include specification and design 1302 of aircraft 1400 in FIG. 14 and material procurement 1304.

During production, component and subassembly manufacturing 1306 and system integration 1308 of aircraft 1400 in FIG. 14 takes place. Thereafter, aircraft 1400 in FIG. 14 may go through certification and delivery 1310 in order to be placed in service 1312. While in service 1312 by a customer, aircraft 1400 in FIG. 14 may be scheduled for routine maintenance and service 1314, which may include modification, reconfiguration, refurbishment, and other maintenance or service.

Each of the processes of aircraft manufacturing and service method 1300 may be performed or carried out by a system integrator, a third party, and/or an operator. In these examples, the operator may be a customer. For the purposes of this description, a system integrator may include, without limitation, any number of aircraft manufacturers and major-system subcontractors; a third party may include, without limitation, any number of vendors, subcontractors, and suppliers; and an operator may be an airline, a leasing company, a military entity, a service organization, and so on.

With reference now to FIG. 14, an illustration of an aircraft is depicted in which an illustrative embodiment may be implemented. In this example, aircraft 1400 may be produced by aircraft manufacturing and service method 1300 in FIG. 13 and may include airframe 1402 with plurality of systems 1404 and interior 1406. Examples of systems 1404 include one or more of propulsion system 1408, electrical system 1410, hydraulic system 1412, and environmental system 1414. Any number of other systems may be included. Although an aerospace example is shown, different illustrative embodiments may be applied to other industries, such as the automotive industry.

Apparatuses and methods embodied herein may be employed during at least one of the stages of aircraft manufacturing and service method 1300 in FIG. 13.

In one illustrative example, components or subassemblies produced in component and subassembly manufacturing 1306 in FIG. 13 may be fabricated or manufactured in a manner similar to components or subassemblies produced while aircraft 1400 may be in service 1312 in FIG. 13.

In one or more illustrative embodiments elongate member bending system 106 may be used to bend elongate members for use in aircraft 1400 during component and subassembly manufacturing 1306. These elongate members may be, for example, stringers, beams, and other suitable structures.

Additionally, elongate member bending system 106 also may be used during other stages of aircraft manufacturing and service method 1300. For example, elongate member bending system 106 may be used during maintenance and service 1314 to bend elongate members that may be used to replace existing elongate members in aircraft 1400 during maintenance of aircraft 1400 in maintenance and service 1314.

As another example, elongate members may be bent during maintenance and service 1314 for use in aircraft 1400 during refurbishment, upgrade, or other operations performed on aircraft 1400. The use of a number of the different illustrative embodiments may substantially expedite the assembly of and/or reduce the cost of aircraft 1400.

Thus, the illustrative embodiments may provide a method and apparatus for bending elongate members, such as stringers. In particular, the illustrative embodiments may be especially useful for bending stringers for use in aircraft. With elongate member bending system 106, elongate members may be processed to have desired bends with a higher rate of output as compared to currently used methodologies for bending stringers. With elongate member bending system 106, the application of plastic force 108 and elastic force 110 may occur without needing input from human operator 138 during the bending of elongate member 112. In some cases, controller 136 may include software that performs operations of repeatedly applying plastic force 108 and elastic force 110 with measurements until elongate member 112 has bent shape 122 in which bend 126 is desired bend 128.

The operations for the process described herein may be repeated until an ideal chord height relating to radius for bend 126 is present in elongate member 112. Because measurement 124 may be made continuously during bending of elongate member 112, a more precise bend control may be realized. Thus, a continuous bend inspection may be performed by elongate member bending system 106. This continuous bend inspection may result in less over-bending, less rework on a part for an aircraft, or both.

Further, manual measurements performed by human operators may be greatly reduced. For example, human operator 138 may only need to release and manually validate the radius of bend 126 once all of the applications of force to elongate member 112 have been completed. As a result, the need for human operator 138 to repeatedly apply force to a stringer, remove the stringer to make measurements, and replace the stringer to apply more force may be avoided.

Thus, with one or more different illustrative embodiments, increased output may be achieved in bending elongate members. Further, with the use of laser measurement systems, reduced fatigue also may occur with respect to human operators. This reduction in fatigue of human operators may result in fewer injuries than with currently used stringer forming systems that use human operators to manually measure the bend of the stringers.

Also, the experience level needed for human operators may be reduced with the use of elongate member bending system 106. As a result, manufacturing an aircraft may be performed more quickly, with less cost, or some combination thereof.

The description of the different illustrative embodiments has been presented for purposes of illustration and description, and is not intended to be exhaustive or limited to the embodiments in the form disclosed. Many modifications and variations will be apparent to those of ordinary skill in the art. Further, different illustrative embodiments may provide different features as compared to other illustrative embodiments. The embodiment or embodiments selected are chosen and described in order to best explain the principles of the embodiments, the practical application, and to enable others of ordinary skill in the art to understand the disclosure for various embodiments with various modifications as are suited to the particular use contemplated.

What is claimed is:

1. A method for bending an elongate member, the method comprising:
    applying a first elastic force to the elongate member before the elongate member is bent by applying a plastic force to the elongate member;
    identifying an amount of deflection of the elongate member while applying the first elastic force;
    applying the plastic force to the elongate member after identifying the amount of deflection, in which the plastic force is configured to cause the elongate member to bend with a plastic deformation;
    reducing the plastic force after the plastic force causes the elongate member to bend with the plastic deformation;
    applying a second elastic force to the elongate member after applying the plastic force to the elongate member;
    identifying a bend of the elongate member while the second elastic force is applied to the elongate member; and
    repeating the steps of applying the plastic force to the elongate member in which the plastic force is configured to cause the elongate member to bend with the plastic deformation, reducing the plastic force after the plastic force causes the elongate member to bend with the plastic deformation, applying the second elastic force to the elongate member after applying the plastic force to the elongate member, and identifying the bend of the elongate member while the second elastic force is applied to the elongate member until the bend of the elongate member is a desired bend for the elongate member.

2. The method of claim 1, wherein identifying the bend of the elongate member while the second elastic force is applied to the elongate member comprises:
    measuring a deflection of the elongate member caused by the plastic force; and
    identifying a radius of the bend using the deflection and a length of the elongate member.

3. The method of claim 1, wherein the plastic force and the first and second elastic forces are applied in a number of locations on the elongate member.

4. The method of claim 1, wherein applying the plastic force comprises:
    applying the plastic force to the elongate member using a press selected from one of a hydraulic press, a pneumatic press, and a mechanical press configured to apply the plastic force and the first and second elastic forces.

5. The method of claim 1, wherein identifying the bend comprises identifying an amount of the bend of the elongate member while the second elastic force is applied to the elongate member using at least one of a laser measurement system and a camera system.

6. The method of claim 1 further comprising:
    selecting the elongate member from one of a stringer, a spar, and a beam.

7. The method of claim 1 further comprising:
    selecting the elongate member for a platform selected from one of a mobile platform, a stationary platform, a land-based structure, an aquatic-based structure, a space-based structure, a surface ship, a tank, a personnel carrier, a train, a spacecraft, a space station, a satellite, a submarine, an automobile, a power plant, a bridge, a dam, a house, a manufacturing facility, and a building.

8. A method for dynamically forming a bend in an elongate member, the method comprising:
    applying a first elastic force to the elongate member before the elongate member is bent by applying a plastic force to the elongate member;
    identifying an amount of deflection of the elongate member while applying the first elastic force;
    applying the plastic force to the elongate member after identifying the amount of deflection, in which the plastic force is configured to cause plastic deformation in the elongate member to form the bend;
    reducing the plastic force to a second elastic force applied to the elongate member to cause elastic deformation in the elongate member;
    measuring the bend while the second elastic force is applied to the elongate member to cause the elastic deformation;
    determining whether the bend in the elongate member is a desired bend; and
    repeating the steps of applying the plastic force to the elongate member, reducing the plastic force to the second elastic force, and measuring the bend while the second elastic force is applied until the bend in the elongate member is the desired bend.

9. The method of claim 8 further comprising:
    measuring a plurality of deflections and an amount of the first elastic force, the plastic force, and the second elastic force, during application of the first elastic force, the plastic force, and the second elastic force on the elongate member to form measurements;
    generating a plot of the measurements; and identifying a number of elastic regions and a number of plastic regions in the plot.

10. The method of claim 9 further comprising:
identifying an amount of the plastic force to apply to the elongate member using the plot with the number of elastic regions and the number of plastic regions.

11. A method for bending a stringer for an aircraft, the method comprising:
applying a first elastic force to an elongate member prior to applying a plastic force to the elongate member;
identifying a bend of the elongate member while the first elastic force is applied to the elongate member prior to applying the plastic force;
applying the plastic force to the elongate member, after identifying the bend, in which the plastic force is configured to cause the elongate member to bend with a plastic deformation;
reducing the plastic force after the plastic force causes the elongate member to bend with the plastic deformation;
applying a second elastic force to the elongate member after applying the plastic force to the elongate member, in which the first elastic force, the plastic force and, the second elastic force are applied in a number of locations on the elongate member; and
repeating the steps of applying the first elastic force to the elongate member prior to applying the plastic force to the elongate member, identifying the bend of the elongate member while the first elastic force is applied to the elongate member, identifying the bend prior to applying the plastic force, applying the plastic force to the elongate member in which the plastic force is configured to cause the elongate member to bend with the plastic deformation, applying the second elastic force to the elongate member after applying the plastic force to the elongate member until the bend of the elongate member is a desired bend for the elongate member.

12. A method for dynamically forming a bend in an elongate member, the method comprising:
applying a first elastic force to an elongate member before the elongate member is bent by applying a plastic force to the elongate member;
identifying a bend in the elongate member while applying the first elastic force to the elongate member;
applying the plastic force to the elongate member configured to cause plastic deformation in the elongate member to form the bend after identifying the bend;
reducing the plastic force applied to the elongate member after the plastic force causes the elastic deformation in the elongate member;
applying a second elastic force to the elongate member after applying the plastic force to the elongate member;
measuring the bend while the second elastic force is applied to the elongate member;
determining whether the bend in the elongate member is a desired bend; and
repeating the steps of applying the plastic force, reducing the plastic force, and measuring the bend until the bend in the elongate member is the desired bend.

13. The method of claim 12 further comprising:
measuring deflection and an amount of the force during application of the force on the elongate member to form measurements;
generating a plot of the measurements;
identifying a number of elastic regions and a number of plastic regions in the plot; and
identifying an amount of the force to apply to the elongate member using the plot with the number of elastic regions and the number of plastic regions.

* * * * *